United States Patent
Wang et al.

(10) Patent No.: US 7,853,050 B2
(45) Date of Patent: Dec. 14, 2010

(54) SYSTEM AND METHOD FOR OPERATION WITHOUT TOUCH BY OPERATORS

(75) Inventors: Hao Wang, Beijing (CN); Ying Huang, Beijing (CN); Yu Xia, Beijing (CN)

(73) Assignees: Vimicro Corporation, Beijing (CN); Wuxi Vimicro Corporation, Jiangsu (CN)

( * ) Notice: Subject to any disclaimer, the term of this patent is extended or adjusted under 35 U.S.C. 154(b) by 936 days.

(21) Appl. No.: 11/419,489

(22) Filed: May 19, 2006

(65) Prior Publication Data

US 2006/0281969 A1    Dec. 14, 2006

(30) Foreign Application Priority Data

Jun. 2, 2005  (CN) ................. 2005 1 0073531

(51) Int. Cl.
G06K 9/00 (2006.01)
H04N 5/225 (2006.01)
G09G 5/00 (2006.01)

(52) U.S. Cl. .............. 382/118; 348/169; 345/156

(58) Field of Classification Search ............ None
See application file for complete search history.

(56) References Cited

U.S. PATENT DOCUMENTS

| | | | | |
|---|---|---|---|---|
| 6,637,883 | B1 * | 10/2003 | Tengshe et al. | 351/210 |
| 6,943,754 | B2 * | 9/2005 | Aughey et al. | 345/8 |
| 7,043,056 | B2 * | 5/2006 | Edwards et al. | 382/103 |
| 7,306,337 | B2 * | 12/2007 | Ji et al. | 351/209 |
| 7,391,888 | B2 * | 6/2008 | Hu et al. | 382/118 |

* cited by examiner

Primary Examiner—Samir A Ahmed
Assistant Examiner—Fred Hu
(74) Attorney, Agent, or Firm—Wuxi Sino IP Agency, Ltd.; Joe Zheng

(57) ABSTRACT

Techniques to control computing systems without the physical touches by operators are disclosed. According to one aspect of the techniques, a non-touch operation system comprises a display unit for displaying operating objects, a capture unit for capturing images of an operator, an image processing unit, a line of sight analysis unit, a notification unit, an action analysis unit and an operation execution unit. The image processing unit is provided for calculating head's position parameters and eye's position parameters according to the captured images. The line of sight analysis unit is provided for determining a watching point of the operator on the display unit according to the calculated head's and eye's parameters and further determining one operating object according to the watching point. The notification unit is provided for informing the operator of the determined operating object in an apperceive way. The action analysis unit is provided for identifying an action of the operator according to one parameter of the calculated head' and eye's position parameters and further determining an action instruction corresponding to the action of the operator. The operation execution unit is provided for executing operation depending on the determined operator object and the determined action instruction.

14 Claims, 4 Drawing Sheets

SYSTEM AND METHOD FOR OPERATION WITHOUT TOUCH BY OPERATORS

BACKGROUND OF THE INVENTION

1. Field of the Invention

The present invention relates to the area of human machine interface. In particular, the present invention is related to system and method for computer operations without touch by operators, and especially to an eye controlled operation.

2. Description of Related Art

Currently, almost all of the computer systems need human direct physical intervention via one or more input devices, examples of the input device may be a mouse, a keyboard or a touch screen etc. However, it is understood such human direct physical intervention makes it easy propagate various diseases or virus should the computer systems be used in public. Furthermore, for those disabled who are at disadvantage of operating manually, it is hard, if not impossible, for them to operate such computer systems.

Canon Corp. has invented a human-machine filming control device. Its principle is that when an infrared beam is projected upon an eyeball looking at an object, an infrared faculae is formed on the corneal of the eyeball. There is a certain angle between the pupil of the eyeball and the infrared faculae in the transversal and vertical directions. This angle would be changed along with turning of the eyeball, namely along with changing of viewing direction. This tiny change value may be obtained from a scanning unit. By comparing the tiny change value with the pre-stored reference values, it can be determined that the human's line of sight is through which auto focus points to watch the object. Thus, the auto focus process is finished. However, the device requires a user or an operator to get so close to a viewfinder of a camera, which, in fact, belongs to a system that still requires direct physical touches by a user. In addition, this device needs an infrared beam generator.

Thus, there is a need for techniques to control computing systems without the physical touches by operators.

SUMMARY OF THE INVENTION

This section is for the purpose of summarizing some aspects of the present invention and to briefly introduce some preferred embodiments. Simplifications or omissions in this section as well as in the abstract or the title of this description may be made to avoid obscuring the purpose of this section, the abstract and the title. Such simplifications or omissions are not intended to limit the scope of the present invention.

In general, the present invention pertains to techniques to control computing systems without the physical touches by operators. Such systems contemplated in the present invention are referred to herein as non-touch operation system. According to one aspect of the techniques, a non-touch operation system comprises a display unit for displaying operating objects, a capture unit for capturing face images of an operator, an image processing unit, a line of sight analysis unit, a notification unit, an action analysis unit and an operation execution unit. The image processing unit is provided for calculating position parameters of the head of the operator and position parameters of the eye(s) of the operator according to the captured face images. The line of sight analysis unit is provided for determining a watching point of the operator on the display unit according to the calculated head's and eye's parameters and further determining one operating object according to the watching point. The notification unit is provided for informing the operator of the determined operating object through a visual interaction. The action analysis unit is provided for identifying an action of the operator according to at least one parameter of the calculated head' and eye's altitude parameters and further determining an action instruction corresponding to the action of the operator. The operation execution unit is provided for executing the operation depending on the determined operator object and the determined action instruction.

According to another aspect of the techniques, a non-touch operation method comprises: capturing face images of an operator; calculating position parameters of the operator's head and position parameters of the operator's one eye according to the captured face images; determining a watching point of the operator on the display unit according to the calculated head's and eye's parameters and further determining one operating object according to the watching point; informing the operator of the determined operating object through a visual interaction; identifying an action of the operator according to at least one parameter of the calculated head' and eye's altitude parameters and further determining an action instruction corresponding to the action of the operator; executing operation depending on the determined operator object and the determined action instruction.

Other objects, features, and advantages of the present invention will become apparent upon examining the following detailed description of an embodiment thereof, taken in conjunction with the attached drawings.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

The detailed description of the present invention is presented largely in terms of procedures, steps, logic blocks, processing, or other symbolic representations that directly or indirectly resemble the operations of units or systems contemplated in the present invention. These descriptions and representations are typically used by those skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments.

Figure 1:
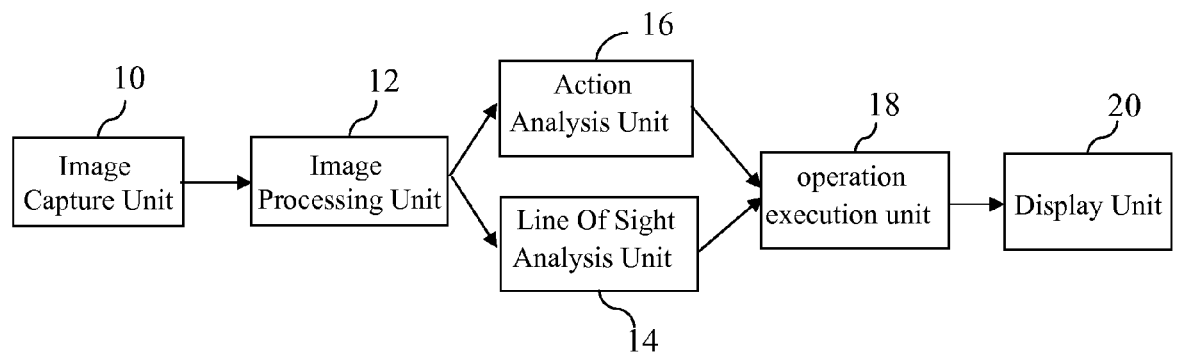
FIG. 1 is a block diagram showing a non-touch operation system of the present invention.

Referring to FIG. 1, it shows a block diagram of an exemplary non-touch operation system according to one embodiment of the present invention. The non-touch operation system includes an image capture unit 10, an image processing unit 12 coupled to the image capture unit 10, a line of sight analysis unit 14 coupled to the image processing unit 12, an action analysis unit 16 coupled to the image processing unit 12, an operation execution unit 18 coupled to the line of sight analysis unit 14 and the action analysis unit 16, a display unit 20 coupled to the operation execution unit 18, and a notification unit (not shown). It should be noted that the image processing unit 12, the line of sight analysis unit 14, the action analysis unit 16, the operation execution unit 18 and the notification unit may be implemented as one or more software modules running on a processor or as an independent hardware circuit outside the processor.

The image capture unit 10 is provided for capturing face images of an operator and providing the captured face images to the image processing unit 12 at a predetermined frame rate, such as 30 frames per second. In one embodiment, a camera with a resolution of 640*480 pixels may be used as the image capture unit 10. The camera can be put on the top of the display unit 20. When the operator sits in front of the display unit 20, the camera is focused on the operator's head to capture the face images.

The image processing unit 12 is provided for calculating head's position parameters and eye's position parameters depending on the face images from the image capture unit 10. In one embodiment, the head's position parameters comprise a pitching parameter related to the head's pitching angle of the operator and a (roll) horizontal turning parameter related to the head's horizontal turning angle of the operator. The eye's position parameters comprise a horizontal watching direction parameter related to the horizontal watching direction of the line of sight of the operator and a vertical watch direction parameter related to the vertical watching direction of the line of sight of the operator. The head's and eye's position parameters could be calculated according to the sizes of the operator's face and eyes, an eye position with respect to the face and a pupil position with respect to the eyes.

According to one embodiment, the image processing unit 12 is first configured to identify the operator's face position and size from every single frame image provided by the image capture unit 10, which could be realized by the conventional face identification technique or other known techniques. Next the image processing unit 12 is configured to further identify the operator's eyes position and size depending on the identified face information, which could be realized by a template matching algorithm or other known methods. Subsequently, the image processing unit 12 identifies the pupil position depending on the identified eyes information, which may be realized by a histogram method.

Figure 2:
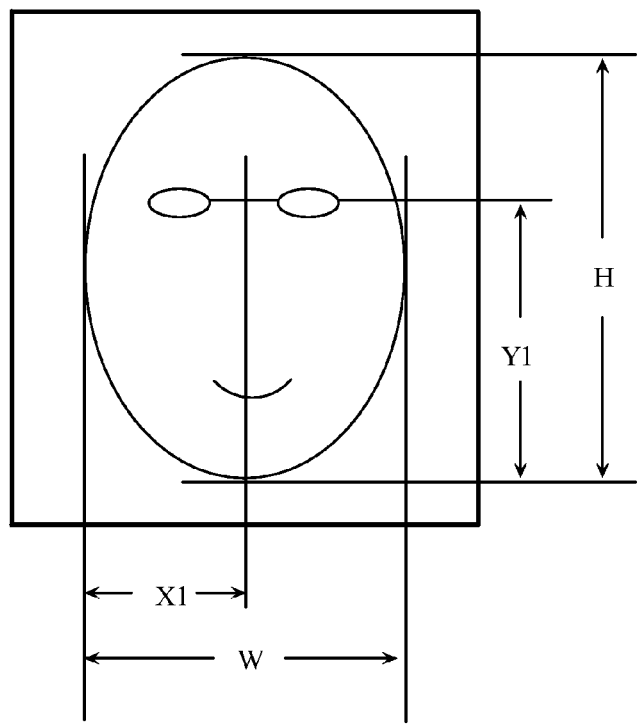
FIG. 2 is a schematic diagram showing operator's face and eyes.

FIG. 2 is a schematic diagram showing the identified operator's face and eyes, wherein the operator's face height identified by the image processing unit 12 is designated as H and the operator's face width identified by the image processing unit 12 is designated as W. Based on the eyes information identified by the image processing unit 12, the center between the eyebrows can be derived. Based on the size of the face, the position of the eyes and the center of the eyebrows, the height Y1 from the eyes to the maxilla and the width X1 from the center between the eyebrows to the left edge of the face can be calculated.

Thus the head's pitching altitude parameter a1 is determined by a1=Y1/H and the head's horizontal turning altitude parameter a2 by a2=X1/W. As the pitching angle being within ±10 degrees, the higher the operator looks the bigger the value of a1 is; contrarily, the smaller the value of a1 is. As the head's horizontal turning angle being within ±30 degrees, the more the operator turns to left the bigger the value of a2 is; or the more the operator turns to right the smaller the value of a2 is.

Figure 3:
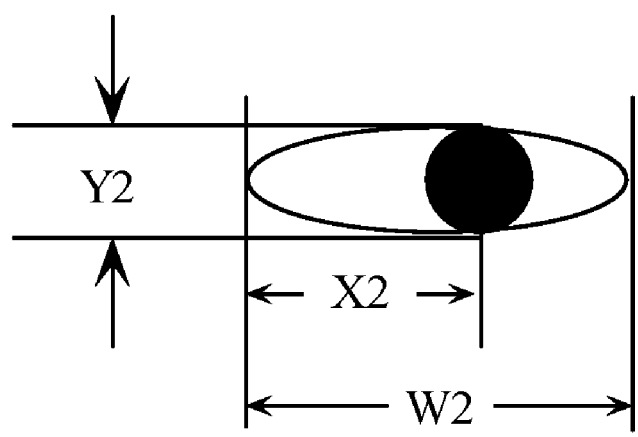
FIG. 3 is a schematic diagram showing operator's eye and pupil.

FIG. 3 is a schematic diagram showing the identified operator's eye and pupil, wherein the operator's eye height identified by the image processing unit 12 is designated as Y2 and the operator's eye width identified by the image processing unit 12 is designated as W2. Based on the position and size of the eye and the position of the pupil, the distance X2 between the center of the pupil and the outboard of the eye can be determined.

Thus the eye's horizontal watching direction parameter a3 by a3=X2/W2 and the eye's vertical watching direction parameter a4 by a4=Y2/W2 can be calculated. The more the eye looks right, the bigger the value a3 is; contrarily, the smaller the value of a3 is. The more the eye looks up the bigger the value a4 is, likewise the more the eye looks down the smaller the value a4 is.

The image processing unit 12 provides the calculated head's position parameters and eye's position parameters, such as parameters a1, a2, a3 and a4, to the line of sight analysis unit 14 and the action analysis unit 16.

The line of sight analysis unit 14 is provided for determining a watching point of the operator on the display unit 20 according to the head's and eye's parameters from the image processing unit 12 and further determining a watching object on the display unit 20.

In a preferred embodiment, a plurality of groups of head's and eye's reference parameters is pre-stored in the line of sight analysis unit 14, each group of which corresponds to one reference point on the display unit 20. Thus, the line of sight analysis unit 14 determines the watching point on the display unit 20 by following operations: matching the calculated head's and eye's parameters with the groups of head's and eye's reference parameters; determining if there is one matched group of head's and eye's reference parameters; if YES, the reference point which the matched group of head's and eye's reference parameters corresponds to will be selected as the watching point; if NO, interpolating the reference points from the groups of head's and eye's reference parameters that are close to the calculated head's and eye's parameters, as a result, the interpolated point will be selected as the watching point.

Figure 4A:
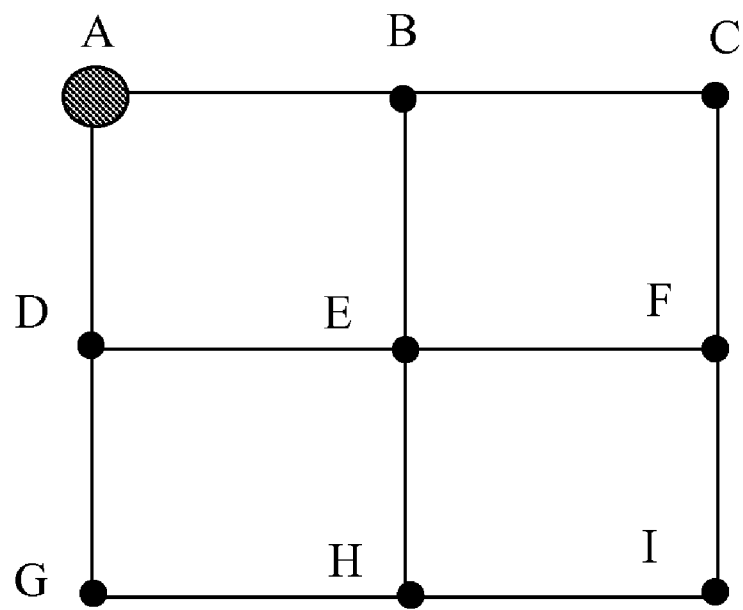
FIG. 4a-c is a block diagram showing a plurality of reference points on a display unit of the non-touch operation system.

To fully understand the present invention, how to get the groups of head's and eye's reference parameters will be illustrated hereafter in conjunction with FIG. 4a, b, c.

Figure 4B:
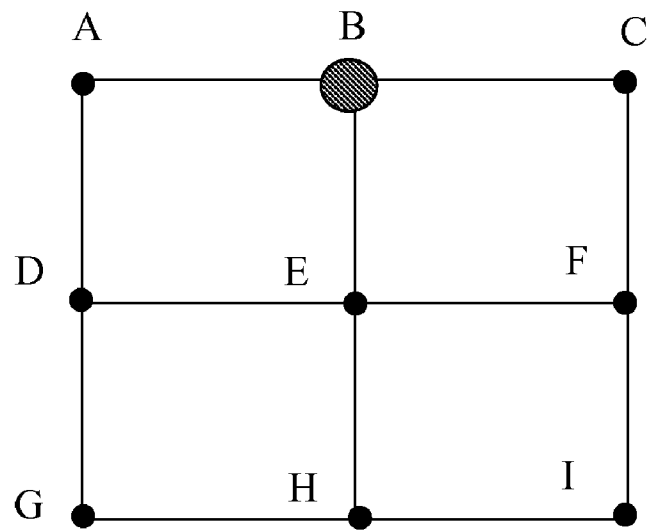
Figure 4C:
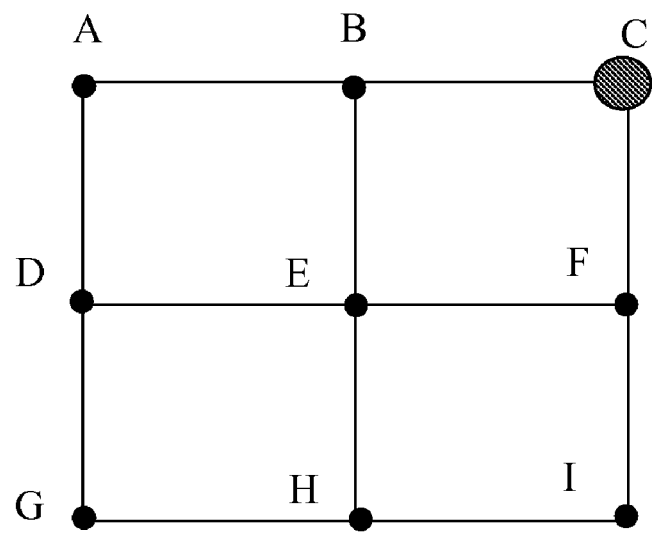

Referring to FIG. 4a-c, there are nine reference points A-I on the display unit 20. It should be noted that the number of reference points may be adjusted depending on implementation. According to one embodiment, a red ball with a diameter of approximate 20 pixels appears at one of the reference points A-I in turn. As shown in FIG. 4a-c, firstly the red ball appears at the reference point A, secondly appearing at the reference point B, thirdly appearing at the reference point C, etc. When the red ball appears at every reference point A-I, the operator keeps watching it in a predetermined time period, such as 3 seconds. During this time period, the image capture unit 10 captures and provides the face images of the operator. Then, the image processing unit 12 is configured to calculate one group of head's and eye's position reference parameters of the operator according to the face images from the image capture unit 10.

Now, taking the reference point A as an example to explain how to get corresponding head's and eye's reference parameters. The image processing unit 12 calculates the head's and eyes altitude parameters for every single frame so that a plurality of groups of head's and eyes altitude parameters are obtained. Taking a1 as an example, as mentioned above, a plurality of head's pitching altitude parameters a1 are obtained. Then, one head's pitching altitude reference parameter a1 is obtained by averaging the plurality of head's pitching altitude parameters a1. Similarly, the reference parameters a2, a3, and a4 are obtained accordingly. Thus, the group of reference parameters a1, a2, a3, and a4 corresponding to the reference point A are obtained. In the same way, the groups of reference parameters a1, a2, a3, and a4 corresponding to the reference points B-I are obtained as well. The image processing unit 12 provides the groups of reference parameters to the line of sight analysis unit 14.

To fully understand the line of sight analysis unit 14, how to match and interpolate the neighbor reference points is discussed hereafter. It should be noted that the head's pitching altitude parameter a1 is not related to the eye's vertical watching direction parameter a4. For example, in order to move the watching point downwardly, the operator may turn the head downwardly with his eyes still, namely, decreasing the parameter a1 with the parameter a4 unchanged; the operator may also look downwardly with his head still, namely, decreasing the parameter a4 with the parameter a1 unchanged; the operator also may simultaneously adjust the parameters a4 and a1. The relationship between the parameters a4 and a1 could be found out by statistics. Similarly, the head's turning altitude parameter a2 is related to the eye's horizontal watching direction parameter a3. The relationship between the parameters a3 and a2 could be found out by statistics.

To facilitate the understanding of the invention, it is assumed that the operator keeps his head still to determine the watching point. Firstly, the line of sight analysis unit 14 determines an X-coordinate of the watching point according to the calculated parameter a3. It is further assumed that the reference parameter a3 of the reference point D is equal to 0.2, the reference parameter a3 of the reference point E is equal to 0.5, the calculated parameter a3 is equal to 0.35, using linear interpolation to calculate the X-coordinate of the watching point can get the interim point between the reference point D and the reference point E. Similarly, the line of sight analysis unit 14 determines a Y-coordinate of the watching point according to the calculated parameter a4.

When the head position parameters are changed too, using the similar method, according to the parameters a1, a2, a3, and a4, and the relationship between a3 and a2, a4 and a1, the line of sight analysis unit 14 determines the coordinates of the watching point of the operator.

Then, the line of sight analysis unit 14 determines the watching object according to the watching point of the operator on the display unit 20 and then provides it to the operation execution unit 18.

The notification unit is provided for informing the operator of the watching object determined by the line of sight analysis unit 14. In one embodiment, after the line of sight analysis unit 14 determines the watching object of the operator, the notification unit 14 darkens the watching object, thereby informing the operator which objects he selects. At this time, the operator could give an action instruction. It should be noted that the notification unit could inform the operator in other way, such as via voice information and etc.

Figure 5:
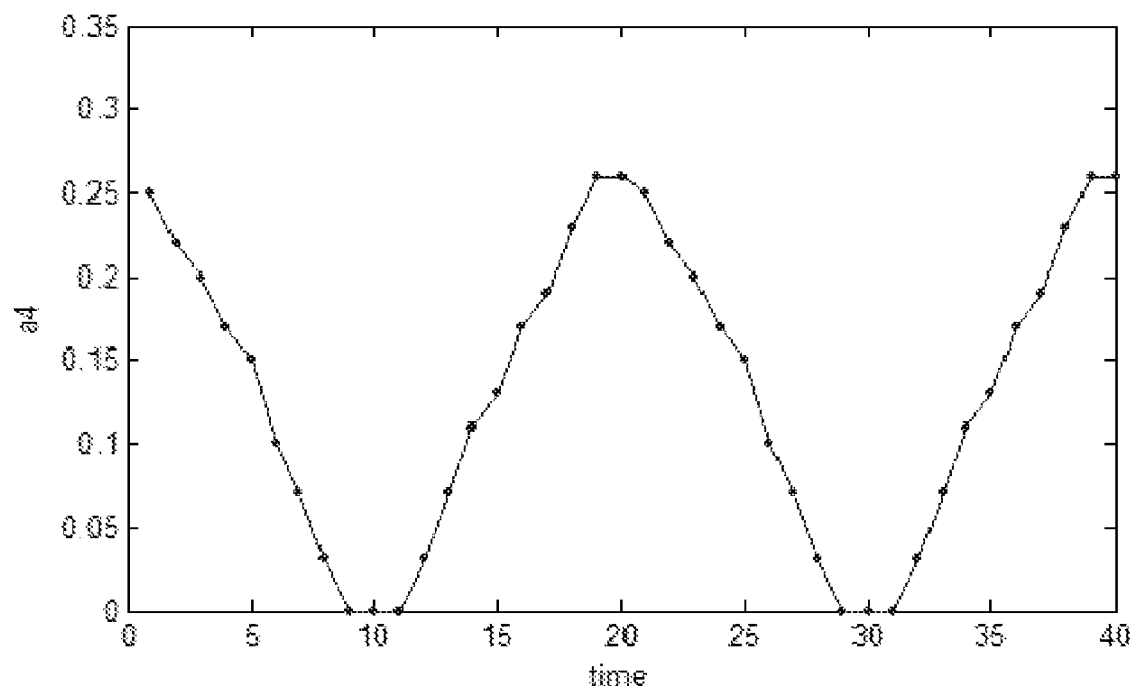
FIG. 5 is a diagram showing a parameter a4 varying along with time when an operator is blinking.
Figure 6:
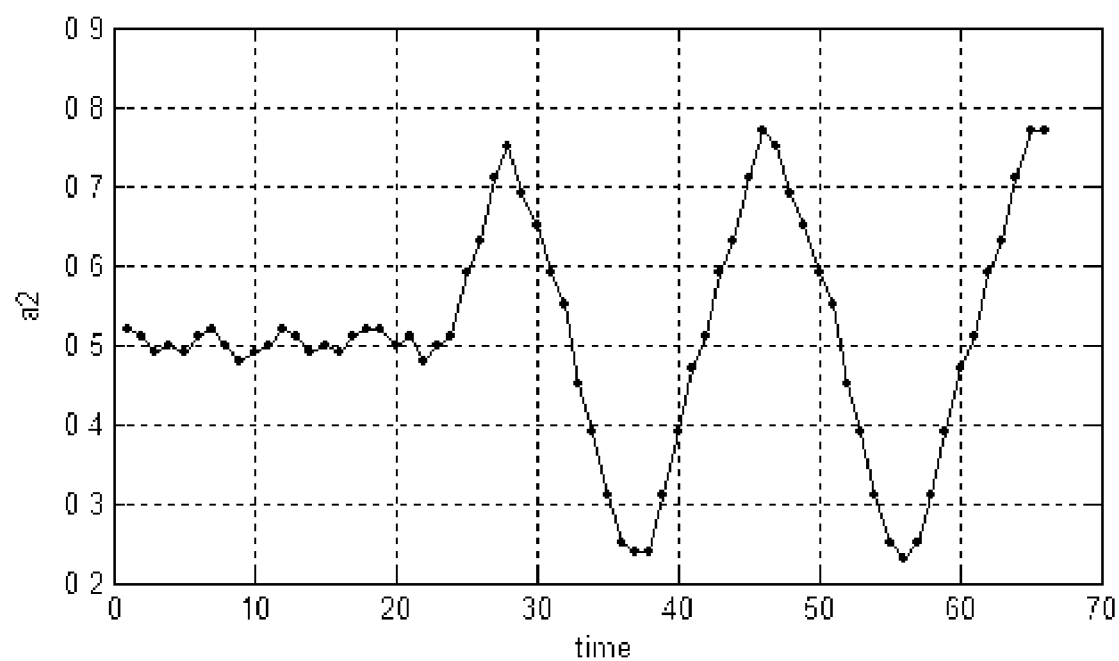
FIG. 6 is a diagram showing a parameter a2 varying along with time when an operator shakes his/her head.

The action analysis unit 16 identifies operator's actions according to the variation of one parameter of the head's and eye's altitude parameters, such as one of parameters a1, a2, a3, and a4, along with time and further determines the action instruction of the operator. As mentioned above, the head's and eye's altitude parameter will be varying with the operator's head altitude and the operator's line of sight. For example, FIG. 5 is a diagram showing the variation of the parameter a4 along with time when the operator is blinking. When the eyes are closed, the value of the parameter a4 gradually decreases until to zero, when the eyes are open, the value of the parameter a4 gradually increases. FIG. 6 is a diagram showing the variation of the parameter a2 along with time when the operator shakes his head. At the beginning, there's no apparently movement, but since the 25th time spot, the parameter a2 appears to have an acute and regular variation. When nodding, the value of parameter a1 has the same change.

The meaning of each operator's action is defined, namely, to define the action instruction represented by each operator's action, such as blinking twice standing for clicking one button, the nod standing for agreement and the shake head standing for disagreement, etc. In one embodiment, a plurality of reference actions and corresponding action instructions in the action analysis unit 16 are pre-stored.

The action analysis unit 16 compares the variation of one parameter of the head' and eye's altitude parameters along with time provided by the image processing unit 12 with the stored operator's reference action to identify the current action of operator. Then, the action analysis unit 16 finds out the action instruction represented by the current action and provide it to the operation execution unit 18.

The operation execution unit 18 is provided for executing operation based on the watch object and the action instruction. The action analysis unit and line of sight analysis unit could work in parallel. Under this condition, in one aspect, the operation execution unit receives the watching object from the line of sight analysis unit 14, in another aspects, the operation execution unit 18 receives the action instruction from the action analysis unit 16. Only when receiving both the watching object and the action instruction, the execution unit 18 could execute the operation.

In one embodiment, the control buttons on the display unit 20 are designed as 30*50 pixels, and separates each other from 30 to 50 pixels.

While the present invention has been described with reference to specific embodiments, the description is illustrative of the invention and is not to be construed as limiting the invention. Various modifications to the present invention can be made to the preferred embodiments by those skilled in the art without departing from the true spirit and scope of the invention as defined by the appended claims.

What is claimed is:

1. A non-touch operation system comprising:
a display unit for displaying operating objects thereon;
a capture unit comprising a camera for capturing images of an entire face on an operator looking at the display unit;
an image processing unit, configured to determine face position and size from each of the images, for calculating position parameters of an eye of the face looking at one of the objects being displayed on the display unit after eye position and size are determined with a template matching technique;
a line of sight analysis unit, coupled to the image processing unit, for storing groups of reference parameters of the face and the eye of the operator, the groups of reference parameters determined separately when a set of preset isolated reference points are sequentially displayed on the display unit, and the line of sight analysis unit configured to compare the calculated position parameters of the face and the eye with the stored groups of reference parameters, and interpolate a watching point of the operator on the display unit;

a notification unit for informing the operator of the object;

an action analysis unit for identifying an action of the operator according to at least one parameter of the calculated position parameters and further determining an action instruction corresponding to the action of the operator; and an operation execution unit for executing an operation depending on the object determined by the line of sight analysis unit and the action instruction determined by the action analysis unit.

2. The non-touch operation system as claimed in claim 1, wherein the action analysis unit is provided for storing a plurality of reference actions, and identifies the action of the operator by matching one or more of the position parameters varying along with time with the stored reference action.

3. The non-touch operation system as claimed in claim 2, wherein the action analysis unit is provided for storing a plurality of instructions corresponding to the reference actions, so that once the action of the operator is determined, one corresponding action instruction is determined.

4. The non-touch operation system as claimed in claim 1, wherein the position parameters pertaining to the face of the operator comprise a pitching parameter related to a head's pitching angle of the operator and a horizontal turning parameter related to a head's horizontal turning angle of the operator.

5. The non-touch operation system as claimed in claim 1, wherein the position parameters pertaining to the operator's eye comprise a horizontal watching direction parameter related to a horizontal watching direction of a line of sight of the operator and a vertical watch direction parameter related to a vertical watching direction of a line of sight of the operator.

6. The non-touch operation system as claimed in claim 1, wherein the image processing unit identifies a face position and a size of the operator's face from every single frame image, and further identifies a position and a size of the operator's one eye depending on the identified face position and size, and still further identifies a pupil position depending on the identified eye position and size, and wherein the image processing unit calculates the head's position parameters according to the identified face position and size as well as the identified eye position and size; the image processing unit calculates some of the position parameters according to the identified eyes position and size as well as the identified pupil position.

7. The non-touch operation system as claimed in claim 1, wherein the notification unit informs the operator of the determined object by darkening the object.

8. A method used in a non-touch operation system, the method comprising:

capturing images of an entire face of an operator;

determining face position and size from each of the images, for calculating position parameters of an eye of the face looking at one of the objects being displayed on the display unit after eye position and size are determined with a template matching technique;

storing groups of reference parameters of the face and eye of the operator, the groups of reference parameters determined separately when a set of preset isolated reference points are sequentially displayed on the display unit;

comparing the calculated position parameters of the face and the eye with the stored groups of reference parameters and interpolating a watching point location on the display unit, and further determining the object according to the watching point;

informing the operator of the determined object;

identifying an action of the operator according to at least one parameter of the calculated position parameters and further determining an action instruction corresponding to the action of the operator; and executing an operation depending on the determined object and the determined action instruction.

9. The method as claimed in claim 8, wherein the non-touch operation system stores a plurality of reference actions, and the identifying of the action of the operator is performed by matching at least one of the position parameters varying along with time with the stored reference action.

10. The method as claimed in claim 8, wherein the non-touch operation system stores a plurality of reference action instructions corresponding to the reference actions.

11. The method as claimed in claim 8, wherein the calculating of the position parameters pertaining to the face and the eye comprises:

identifying an operator's face position and size from every single frame image;

further identifying an operator's eye position and size depending on the identified face position and size;

identifying a pupil position depending on the identified eye position and size;

calculating the face position parameters according to the identified face position and size as well as the identified eyes position and size information, and the eye's position parameters according to the identified eye position and size as well as the identified pupil position.

12. The method as claimed in claim 8, wherein the position parameters pertaining to the face of the operator comprise a pitching parameter related to a head's pitching angle and a horizontal turning parameter related to a head's horizontal turning angle of the operator.

13. The non-touch operation method as claimed in claim 8, wherein the position parameters pertaining to the operator's one eye comprise a horizontal watching direction parameter related to a horizontal watching direction of a line of sight of the operator and a vertical watch direction parameter related to a vertical watching direction of a line of sight of the operator.

14. The method as claimed in claim 8, further comprising darkening the object as displayed.

* * * * *